US012624195B2

(12) United States Patent
Wang et al.

(10) Patent No.: US 12,624,195 B2
(45) Date of Patent: May 12, 2026

(54) HYDROXYBUTYL CHITIN, HYDROXYBUTYL CHITIN HYDROGEL AND PREPARATION METHODS THEREOF

(71) Applicant: Hangzhou Singclean Medical Products Co., Ltd, Hangzhou (CN)

(72) Inventors: Jue Wang, Hangzhou (CN); Jie Zheng, Hangzhou (CN); Xingyu Liu, Hangzhou (CN); Meiqin Zhu, Hangzhou (CN); Qianqian Jia, Hangzhou (CN)

(73) Assignee: Hangzhou Singclean Medical Products Co., Ltd, Hangzhou (CN)

( * ) Notice: Subject to any disclaimer, the term of this patent is extended or adjusted under 35 U.S.C. 154(b) by 609 days.

(21) Appl. No.: 18/147,703

(22) Filed: Dec. 29, 2022

(65) Prior Publication Data

US 2023/0383099 A1     Nov. 30, 2023

(30) Foreign Application Priority Data

May 31, 2022    (CN) .......................... 202210610383.9

(51) Int. Cl.
| | |
|---|---|
| C08B 37/08 | (2006.01) |
| A61L 27/20 | (2006.01) |
| A61L 27/52 | (2006.01) |
| A61L 27/54 | (2006.01) |
| C08J 3/075 | (2006.01) |
| C08L 5/08 | (2006.01) |
| C12N 5/00 | (2006.01) |

(52) U.S. Cl.
CPC ................ *C08L 5/08* (2013.01); *A61L 27/20* (2013.01); *A61L 27/52* (2013.01); *A61L 27/54* (2013.01); *C08B 37/003* (2013.01); *C08J 3/075* (2013.01); *C12N 5/0018* (2013.01); *A61L 2430/34* (2013.01); *C08J 2305/08* (2013.01); *C12N 2500/34* (2013.01)

(58) Field of Classification Search
CPC ....... C08B 37/003; C08J 2305/08; C08L 5/08
See application file for complete search history.

(56) References Cited

FOREIGN PATENT DOCUMENTS

WO      WO-2015161814 A1 * 10/2015     ............. A61K 47/36

OTHER PUBLICATIONS

Sun, Mengjie et al., Biomacromolecules, "Hydroxybutyl Chitosan Centered Biocomposites for Potential Curative Applications: A Critical Review", 2020, vol. 21, pp. 1351-1367 (Year: 2020).*
Bi, Schichao et al., Carbohydrate Polymers, "Temperature responsive self-assembled hydroxybutyl chitosan nanohydrogel based on homogeneous reaction for smart window", 2020, vo. 229, p. 115557 (Year: 2020).*
Bi, Shichao et al., Green Chemistry, "Homogeneous modification of chitin and chitosan based on an alkali/urea soluble system and their applications in biomedical engineering", 2021, vol. 23, pp. 9318 (Year: 2021).*
Cai, Yan et al., Carbohydrate Polymers, "Thermo-responsive behaviors and bioactivities of hydroxybutyl chitosans prepared in alkali/urea aqueous solutions", 2019, vol. 215, pp. 90-98 (Year: 2019).*
Liu, Yi et al., Carbohydrate Polymers, "Versatile synthesis, characterization and properties of beta-chitin derivatives from aqueous KOH/urea solution", 2020, vol. 227, pp. 115345; Retracted (Year: 2020).*
Su, J.C. et al., Journal of Thermal Analysis and Calorimetry, "Effect of SDS on the Gelation of Hydroxypropylmethylcellulose Hydrogels", 2008, vol. 93, pp. 495-501 (Year: 2008).*

* cited by examiner

*Primary Examiner* — Bahar Craigo

(57) ABSTRACT

Disclosed in the present disclosure are a hydroxybutyl chitin, a hydroxybutyl chitin hydrogel and a preparation method thereof. Chitin is subjected to pulverization, dissolution, modification with epoxybutane, and purification to obtain a final product, namely the hydroxybutyl chitin. The hydroxybutyl chitin prepared by the method has good solubility in purified water, and a hydrogel with a low solid content can be formed. The hydroxybutyl chitin hydrogel will have a wide application aspect in biomedicine, absorbable materials, and other fields.

5 Claims, 3 Drawing Sheets

HYDROXYBUTYL CHITIN, HYDROXYBUTYL CHITIN HYDROGEL AND PREPARATION METHODS THEREOF

CROSS-REFERENCE TO RELATED APPLICATION

The present application claims priority from Chinese Patent Application No. 202210610383.9 filed on May 31, 2022, the contents of which are incorporated herein by reference in their entirety.

TECHNICAL FIELD

The present disclosure belongs to the technical field of materials, and relates to a hydroxybutyl chitin hydrogel and a preparation method thereof.

BACKGROUND

Chitin is a natural linear polysaccharide polymer with 2-acetylamino-(1,4)-β-glucose as a repeating unit. The chitin is widely found in nature, and mainly derived from shells of fishes, shrimps, crabs and other animals and cell walls of fungi. The chitin is a nitrogen-containing organic substance with the largest number in nature, and also one of polymers with the highest content in nature. The chitin has many excellent properties, such as excellent biocompatibility, low immunogenicity, and good hemostatic property. Thus, the chitin has a broad application prospect in biomedicine, absorbable materials, and other fields.

A chitin derivative hydrogel is an excellent absorbable material. Due to the interaction of intramolecular or inter-molecular sugars of the chitin, a hydrogen bond and a linear molecular structure likely to induce dense molecular stacking, the chitin has poor solubility. Most of structural materials like carapaces are found in nature. When the chitin is modified with some reagents, the dense molecular packing capacity of a chitin derivative is reduced, and the water solubility is improved. The balance of the hydrophilicity and hydrophobicity of a chitin derivative molecule can be adjusted by changing the type and amount of the reagents to obtain a chitin derivative hydrogel. Two common chitin modification reagents include a halogenated hydrocarbon reagent and an epoxy reagent. The halogenated hydrocarbon reagent includes chloroacetic acid, chloroethanol and the like. Carboxymethyl chitin and hydroxyethyl chitin are obtained after a substitution reaction of hydroxyl of the chitin. The common epoxy reagent includes propylene oxide and the like, and an obtained derivative is hydroxypropyl chitin.

Hydrogel can be formed by the above chitin derivatives through physical crosslinking, and the hydrogel has become one of research hotspots at present.

SUMMARY

Objectives of the present disclosure are to find a novel chitin derivative and explore a novel chitin hydrogel. A prepared hydroxybutyl chitin has good dispersibility in an aqueous phase, can be prepared into a physical hydrogel, and has a wide application prospect in tissue engineering, cell culture, Class III medical apparatuses and instruments, and other aspects. Therefore, based on research conducted by the inventor and experimental results, the following technical schemes are proposed.

According to a first aspect of the present disclosure, the following technical solutions are used in the present disclosure.

A method for preparing a hydroxybutyl chitin, including the following steps:

(1) subjecting chitin to standing and dispersion in an alkaline aqueous solution at low temperature;

(2) adding epoxybutane or diluted epoxybutane to a chitin aqueous phase system, and conducting stirring for a reaction; and (3) after the reaction is completed, conducting dialysis and freeze-drying to obtain the hydroxybutyl chitin.

On the basis of the above technical scheme, the following further technical schemes may also be adopted or combined in the present disclosure to form different kinds of further optimized technical schemes.

In step (1), a chitin powder is added to the alkaline aqueous solution for treatment at −20° C. to room temperature for 1-30 days.

In step (2), before being added to the chitin alkaline aqueous solution, the epoxybutane is diluted with a mixed reagent to adjust a gelatination effect of the hydroxybutyl chitin. The mixed reagent includes one or more of methanol, ethanol, isopropanol and n-butanol (all alcohol reagents preferably account for 20%-80% of a volume fraction of the mixed reagent), purified water (preferably accounting for 20%-80% of the volume fraction of the mixed reagent), one or more of sodium dodecyl sulfate, sodium iodide and potassium iodide (preferably having a total concentration of 0-0.1 g/mL in the mixed reagent), and one or more of lithium chloride, sodium chloride, potassium chloride and cesium chloride (preferably having a total concentration of 0-0.1 g/mL in the mixed reagent). A method for preparing the mixed agent includes: adding the alcohol reagent, the puri-fied water, and the salt reagent to the epoxybutane in sequence, and conducting stirring uniformly for use.

In step (2), the epoxybutane or the diluted epoxybutane is added to the chitin alkaline aqueous solution, and stirred for a reaction at 0° C.-45° C. for 1-7 days.

In step (3), after the reaction is completed, the system is diluted 1-20 times with purified water, followed by dialysis and freeze-drying.

According to a second aspect of the present disclosure, the following technical solutions are used in the present disclosure.

A method for preparing a hydroxybutyl chitin hydrogel, including the following preparation steps:

adding the hydroxybutyl chitin prepared by any one of the above preparation methods to purified water, and conducting stirring at 0° C.-30° C. for complete dissolution to form the hydroxybutyl chitin hydrogel.

According to a third aspect of the present disclosure, the following technical solutions are used in the present disclosure.

A hydroxybutyl chitin, being prepared by the preparation method including the above preparation steps.

According to a fourth aspect of the present disclosure, the following technical solutions are used in the present disclosure.

A hydroxybutyl chitin hydrogel, being prepared by the preparation method including the above steps.

In the present disclosure, the inventor has tried to modify the chitin with the epoxybutane, and the hydroxybutyl chitin and the hydrogel thereof are prepared. Compared with reported chitin modification reagents, the epoxybutane has higher hydrophobicity, and is suitable for modifying poly-mers (such as chitosan) that are more hydrophilic than the chitin. There are more difficulties in a chitin modification reaction and purification of a product, such as phase separation in a reaction and uncontrollable precipitation in purification. However, adjusting the balance of the hydrophilicity and hydrophobicity of a chitin derivative is considered, the hydroxybutyl chitin and the hydrogel thereof have nevel properties. The research of the hydroxybutyl chitin and the hydrogel thereof is of great significance for further exploring a gelatination mechanism of a physical hydrogel, discovering a novel chitin modification method and finding properties of a novel chitin derivative hydrogel.

A product of the hydroxybutyl chitin of the present disclosure is a white spongy solid, and is likely to absorb moisture. According to an experiment, it is proven that the hydroxybutyl chitin of the present disclosure has good dispersibility in purified water, and has a solid content of 2.0% to 2.5%.

The present disclosure is further described below with reference to the accompanying drawings and embodiments.

DETAILED DESCRIPTION

Figure 1:
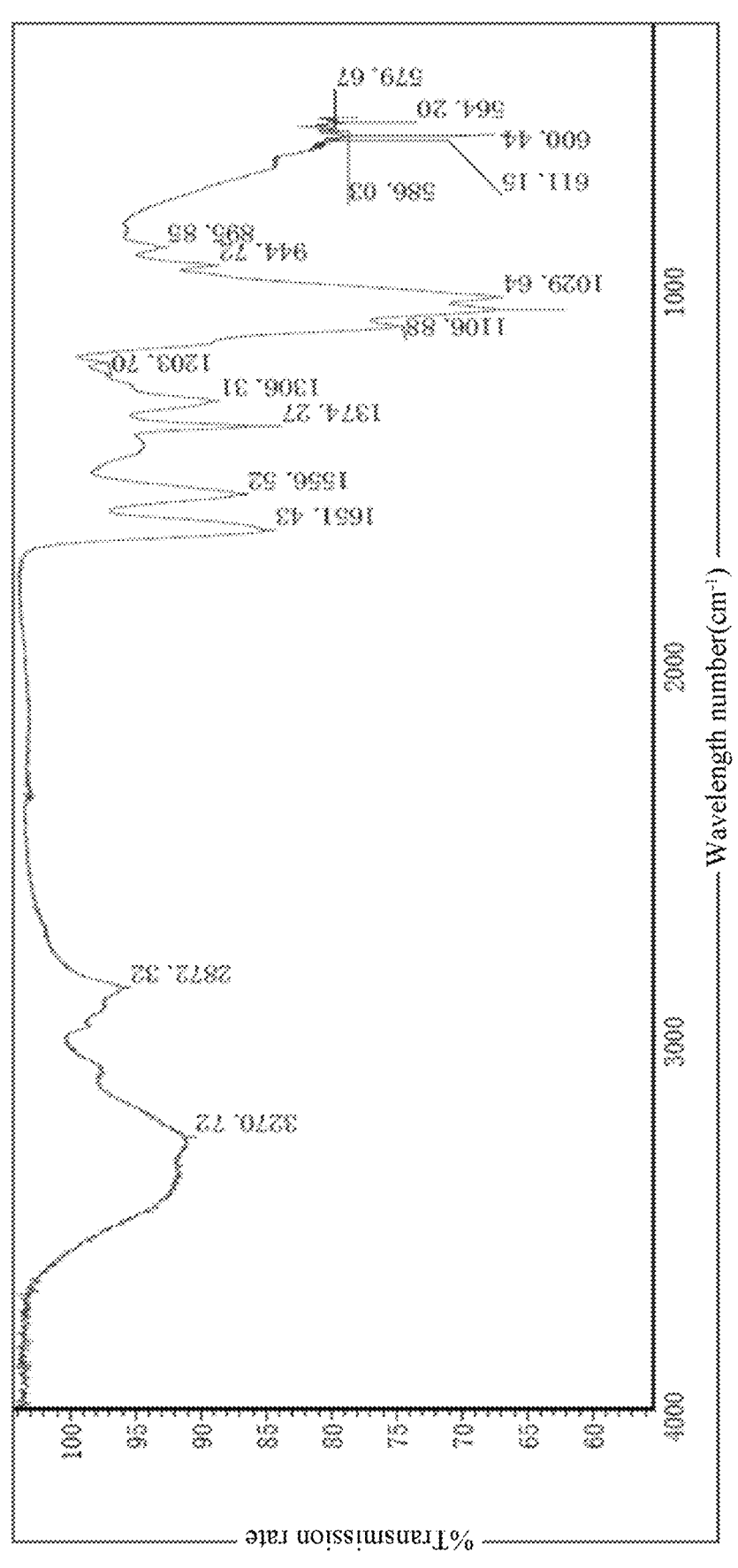
FIG. 1 is a diagram showing the infrared spectrum of a hydroxybutyl chitin prepared in the present disclosure.

In order to further understand the present disclosure, a preparation method of highly dispersed chitin in aqueous phase provided in the present disclosure will be specifically described below with reference to embodiments. But the present disclosure is not limited to these embodiments. Non-essential improvements and adjustments made by a person skilled in the art under the core guiding ideology of the present disclosure still fall within the protection scope of the present disclosure.

Example 1 Preparation of a Chitin Solution (1) Preparation of a chitin powder 20.00 g of chitin was weighed, and put in a Chinese medicine pulverizer for grinding for 2-5 minutes. Ground chitin was taken out, and sequentially sifted through a 20-mesh sieve and a 50-mesh sieve to obtain a chitin powder.

(2) Preparation of an alkaline aqueous solution 129.42 g of NaOH was accurately weighed, and slowly added to 1 L of purified water for several times. After the NaOH was completely dissolved and the temperature of the system was lowered to normal temperature, 47.06 g of urea was added to an obtained solution, stirred for dissolution, and cooled to room temperature.

(3) Dissolution and dispersion of the chitin powder 1.85 g of the chitin powder was added to 1 L of the alkaline aqueous solution, and stirred for dispersion. The whole system was soaked in a low-temperature medium for treatment at −2° C. for 24 hours. The system was taken out, recovered to room temperature, stirred for 1 hour, and then soaked in a low-temperature medium for standing at a low temperature of −20° C. for 20 days. The system was taken out, and recovered to room temperature to obtain a chitin alkaline aqueous solution with good dispersibility and high viscosity.

Example 2 Preparation of Hydroxybutyl Chitins 4 kinds of chitin modification reagents were prepared by changing a volume ratio of epoxybutane to a mixed reagent. The 4 kinds of reagents sequentially include: a modification reagent 1 (including the epoxybutane with a volume ratio of 100% and the mixed reagent with a volume ratio of 0%), a modification reagent 2 (including the epoxybutane with a volume ratio of 75% and the mixed reagent with a volume ratio of 25%), a modification reagent 3 (including the epoxybutane with a volume ratio of 25% and the mixed reagent with a volume ratio of 75%), and a modification reagent 4 (including the epoxybutane with a volume ratio of 0% and the mixed reagent with a volume ratio of 100%).

The mixed reagent includes the following ratios of components: an alcohol reagent accounting for 60% of a volume of the mixed reagent (the volume ratio of each reagent to the mixed reagent is as follows), including 20% of isopropanol, 20% of ethanol, and 20% of methanol; purified water with a volume ratio of 40%; sodium chloride with a concentration of g/mL; and sodium iodide with a concentration of 0.01 g/mL.

With the modification reagent 2 as an example, a method for preparing the reagent is as follows. 30 mL of epoxybutane was accurately weighed, and 2 mL of isopropanol, 2 mL of ethanol, and 2 mL of methanol were sequentially added, and stirred uniformly. 0.1 g of sodium chloride and 0.1 g of sodium iodide were weighed, sequentially added to 4 mL of purified water, and stirred for dissolution. A purified aqueous solution of the sodium chloride and the sodium iodide was dropped to a mixed solution of the epoxybutane and the alcohols, and stirred uniformly to obtain the mixed reagent 2. The modification reagents 1-4 were prepared according to the above method.

The 4 kinds of modification reagents (with 5 mL of each reagent) were separately dropped to 50 mL of the chitin solution prepared in Example 1, and stirred for a reaction at 4° C. for 2 days. A corresponding relationship between the modification reaction and resulting products is as follows: the product modified with the modification reagent 1 is a hydroxybutyl chitin 1, the product modified with the modification reagent 2 is a hydroxybutyl chitin 2, the product modified with the modification reagent 3 is a hydroxybutyl chitin 3, and the product modified with the modification reagent 4 is a hydroxybutyl chitin 4.

Example 3 Purification of a Hydroxybutyl Chitin (1) An aqueous phase system in Example 2 was taken out, and 150 mL of purified water was added and stirred uniformly.

(2) An insoluble substance in the system was filtered out, and the system was subjected to dialysis with a cellulose ester dialysis bag to remove low molecular polysaccharide below 5,000 Da, where 5 L of purified water was used for the dialysis each time. The water was continuously changed every 4 hours for 4 times, and then continuously changed every 12 hours for 6 times.

(3) After the dialysis was completed, a liquid in the bag was taken out, and freeze-dried to obtain a hydroxybutyl chitin. Infrared data of the hydroxybutyl chitin 2 are as shown in FIG. 1.

Example 4 Preparation of Hydroxybutyl Chitin Hydrogel

Certain amounts of the 4 kinds of hydroxybutyl chitins were weighed, and 3.5 mL of purified water was added. 4 kinds of hydroxybutyl chitin systems with a mass fraction of 1%, 2%, and 2.5% were separately prepared. The systems were shaken at room temperature for 3 minutes, and put in a refrigerator for standing at 4° C. for 0.5 hour. Samples were taken out, and stirred at 4° C. for 15 hours to obtain stable hydroxybutyl chitin aqueous phase systems. The time for dissolution and dispersion of the hydroxybutyl chitin 1 is longer than 12 hours, and the time for dispersion and dissolution of other hydroxybutyl chitins is 5-8 hours.

Figure 2:
FIG. 2 is an effect diagram showing aqueous phase systems of 4 kinds of hydroxybutyl chitins with a mass fraction of 1%. From left to right, a hydroxybutyl chitin 1, a hydroxybutyl chitin 2, a hydroxybutyl chitin 3, and a hydroxybutyl chitin 4 are shown in sequence.
Figure 2:

As shown in FIG. 2, when the mass fraction is 1%, a viscous liquid is formed by the hydroxybutyl chitin 1, and solutions with good fluidity are formed by the hydroxybutyl chitins 2, 3, and 4. After placement at room temperature for 14 days, a flocculent precipitate is formed in the hydroxybutyl chitin 4 system.

Figure 3:
FIG. 3 is an effect diagram showing aqueous phase systems of 4 kinds of hydroxybutyl chitins with a mass fraction of 2%. From left to right, a hydroxybutyl chitin 1, a hydroxybutyl chitin 2, a hydroxybutyl chitin 3, and a hydroxybutyl chitin 4 are shown in sequence.

As shown in FIG. 3, when the mass fraction is 2%, hydrogel is formed by the hydroxybutyl chitins 1 and 2, and solutions with good fluidity are formed by the hydroxybutyl chitins 3 and 4. The time for dispersion of the hydroxybutyl chitin 1 is long (about 12 hours). After placement at room temperature for 14 days, a small amount of purified water permeates through the hydroxybutyl chitin 1 hydrogel, and the gel has low stability; and a flocculent precipitate is formed in the hydroxybutyl chitin 4 system.

Figure 4:
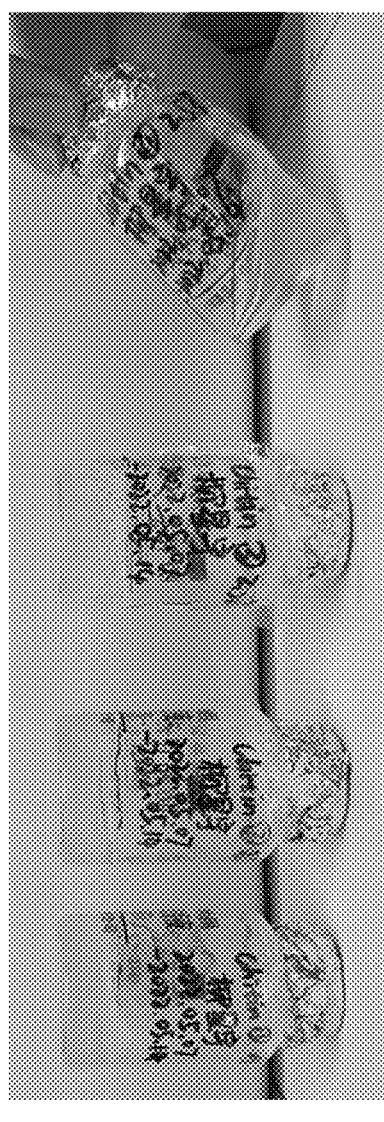
FIG. 4 is an effect diagram showing aqueous phase systems of 4 kinds of hydroxybutyl chitins with a mass fraction of 2.5%. From left to right, a hydroxybutyl chitin 1, a hydroxybutyl chitin 2, a hydroxybutyl chitin 3, and a hydroxybutyl chitin 4 are shown in sequence.

As shown in FIG. 4, when the mass fraction is continuously increased to 2.5%, hydrogel is formed by the hydroxybutyl chitins 1, 2, and 3, and a solution with good fluidity is formed by the hydroxybutyl chitin 4. The time for dispersion of the hydroxybutyl chitin 1 is still long (about 12 hours). After placement at room temperature for 14 days, a small amount of purified water permeates through the hydroxybutyl chitin 1 hydrogel, and the gel has unsatisfactory stability; and a flocculent precipitate is formed in the hydroxybutyl chitin 4 system.

The dispersion time, solid content, and hydrogel stability of the hydroxybutyl chitins are comprehensively considered, the hydroxybutyl chitin 2 has better performance. When the solid content is 2%-2.5%, a hydroxybutyl chitin hydrogel is formed in 5-8 hours.

CONCLUSION

In the present disclosure, the chitin is dispersed to obtain a chitin alkaline aqueous phase system with good dispersibility. The chitin is modified by adding the epoxybutane or the diluted epoxybutane. A novel hydroxybutyl chitin is obtained by dilution, dialysis, and freeze-drying of a sample system. A uniform and stable physical cross-linked hydrogel can be formed by the hydroxybutyl chitin with a solid content of 2%-2.5%. The hydroxybutyl chitin hydrogel will be further developed into a novel tissue engineering scaffold and other degradable materials to play an important role in the field of Class III medical apparatuses and instruments.

What is claimed is:

1. A method for preparing a hydroxybutyl chitin, comprising the following steps:
    (1) dispersing chitin in an alkaline aqueous solution at a temperature within a range of −20° C to −2° C to obtain a chitin alkaline aqueous solution;
    (2) adding epoxybutane to the chitin alkaline aqueous solution, and stirring for a reaction,
    wherein before being added to the chitin alkaline aqueous solution, the epoxybutane is diluted with a mixed reagent comprising
    i) one or more alcohol reagents selected from the group consisting of methanol, ethanol, isopropanol and n-butanol;
    ii) purified water;
    iii) one or more selected from the group consisting of sodium dodecyl sulfate, sodium iodide and potassium iodide; and
    iv) one or more selected from the group consisting of lithium chloride, sodium chloride, potassium chloride and cesium chloride; and
    (3) after the reaction is completed, conducting dialysis and freeze-drying to obtain the hydroxybutyl chitin.

2. The method for preparing a hydroxybutyl chitin according to claim 1, wherein in step (2), the epoxybutane is added to the chitin alkaline aqueous solution, and stirred for a reaction at 0° C.-45° C. for 1-7 days.

3. The method for preparing a hydroxybutyl chitin according to claim 1, wherein the one or more alcohol reagents account for 20%-80% of a volume fraction of the mixed reagent; the purified water accounts for 20%-80% of the volume fraction of the mixed reagent; the one or more of the sodium dodecyl sulfate, the sodium iodide and the potassium iodide have a total concentration of 0.01-0.1 g/mL in the mixed reagent; and the one or more of the lithium chloride, the sodium chloride, the potassium chloride and the cesium chloride have a total concentration of 0.01-0.1 g/mL in the mixed reagent.

4. The method for preparing a hydroxybutyl chitin according to claim 1, wherein in step (3), after the reaction is completed, the chitin alkaline aqueous solution is diluted 1-20 times with purified water, followed by dialysis and freeze-drying.

5. A method for preparing a hydroxybutyl chitin hydrogel, comprising the following preparation steps:
    adding the hydroxybutyl chitin prepared by the preparation method according to claim 1 to purified water, and conducting stirring at 0° C.-30° C. for complete dissolution to form the hydroxybutyl chitin hydrogel.

* * * * *